(12) United States Patent
Roberts et al.

(10) Patent No.: US 6,692,445 B2
(45) Date of Patent: Feb. 17, 2004

(54) BIOPSY SAMPLER

(75) Inventors: Troy W. Roberts, Pepperell, MA (US); Bruce H. Diamond, Wellesley, MA (US); William J. Shaw, Cambridge, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 102 days.

(21) Appl. No.: 09/905,200

(22) Filed: Jul. 16, 2001

(65) Prior Publication Data

US 2002/0049442 A1 Apr. 25, 2002

Related U.S. Application Data

(63) Continuation-in-part of application No. 09/361,532, filed on Jul. 27, 1999, now Pat. No. 6,261,242.

(51) Int. Cl.$^7$ .......................... A61B 10/00; A61B 18/18; A61B 17/32
(52) U.S. Cl. .......................... 600/564; 606/47; 606/170
(58) Field of Search .............................. 607/96, 98, 99, 607/101, 115, 116; 606/27, 28, 29, 30, 40, 41, 42–50; 604/205; 600/562–570

(56) References Cited

U.S. PATENT DOCUMENTS

| 3,892,228 A | 7/1975 | Mitsui |
| 4,674,499 A | 6/1987 | Pao |
| 4,953,559 A | 9/1990 | Salerno |
| 5,085,659 A | 2/1992 | Rydell |
| 5,171,255 A | 12/1992 | Rydell |
| 5,258,006 A | 11/1993 | Rydell et al. |
| 5,336,222 A | 8/1994 | Durgin, Jr. et al. |
| 5,352,222 A | 10/1994 | Rydell |
| 5,352,234 A | 10/1994 | Scott |
| 5,352,235 A | 10/1994 | Koros et al. |
| 5,364,395 A | 11/1994 | West, Jr. |
| 5,394,885 A | 3/1995 | Francese |
| 5,403,311 A | 4/1995 | Abele et al. |
| 5,409,453 A | 4/1995 | Lundquist et al. |
| 5,470,308 A | 11/1995 | Edwards et al. |
| 5,507,743 A | 4/1996 | Edwards et al. |
| 5,522,815 A | 6/1996 | Durgin, Jr. et al. |
| 5,578,030 A | 11/1996 | Levin |
| 5,607,389 A | 3/1997 | Edwards et al. |
| 5,928,163 A | 7/1999 | Roberts et al. |
| 6,162,216 A | 12/2000 | Guziak et al. |
| 6,214,024 B1 | 4/2001 | Houser |
| 6,261,242 B1 | 7/2001 | Roberts et al. |
| 6,306,132 B1 | 10/2001 | Moorman et al. |

Primary Examiner—Max Hindenburg
Assistant Examiner—David J. McCrosky
(74) Attorney, Agent, or Firm—Fulbright & Jaworski L.L.P.

(57) ABSTRACT

The invention features an assembly for taking a biopsy sample from a site within the body of a patient. The assembly includes a resecting device having a cutter near its distal end for resecting and containing a tissue sample and a sheath exterior to the resecting device and sized to be present within the body with the resecting device. The sheath includes an electrode element electrically isolated from the resecting device and disposed on the sheath's outer surface for cauterizing tissue. The electrode element may reside on the outer sheath, the distal end or both the outer sheath and the distal end of the assembly. The resecting device and the sheath cooperate to permit sequential resecting of a tissue sample from a resecting site and cauterizing of the site with the cutter sufficiently spaced from the electrode element to avoid heat damage to the tissue sample.

5 Claims, 13 Drawing Sheets

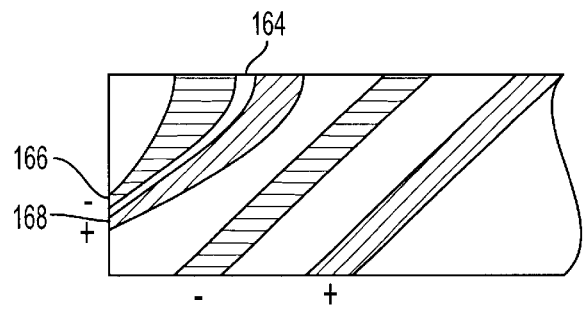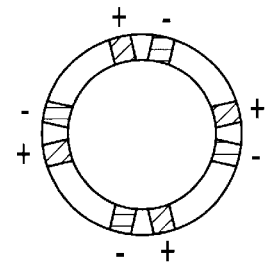
FIG. 10A  FIG. 10B
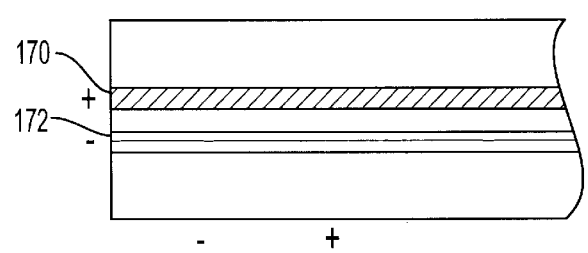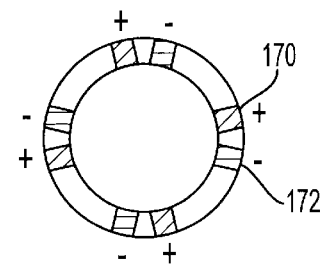
FIG. 11A  FIG. 11B
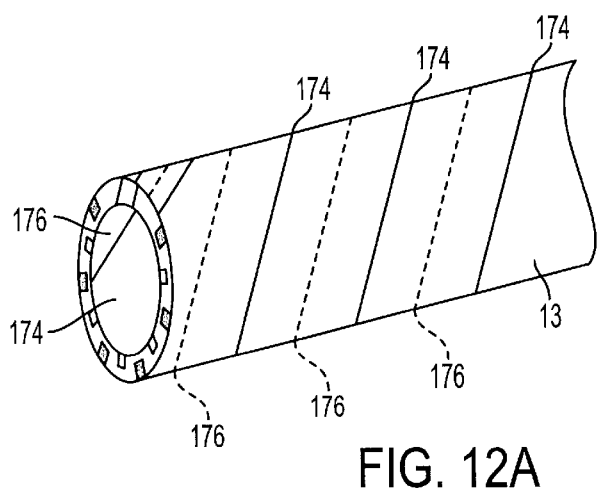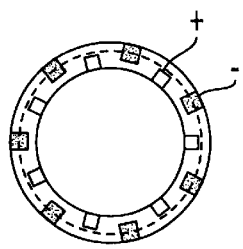
FIG. 12A  FIG. 12B

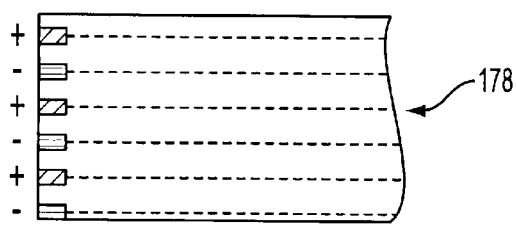
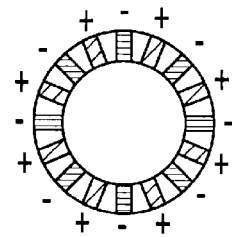
FIG. 13A     FIG. 13B
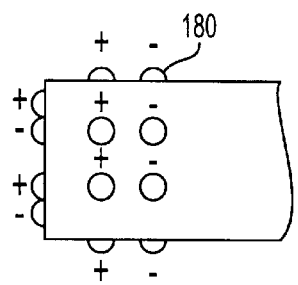
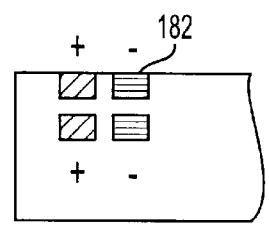
FIG. 14     FIG. 15
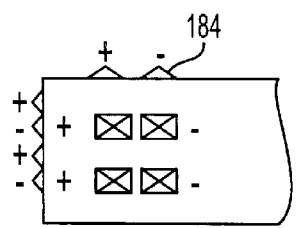
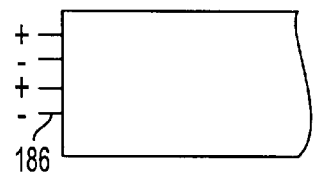
FIG. 16     FIG. 17

BIOPSY SAMPLER

CROSS-REFERENCE TO RELATED APPLICATIONS

This application is a continuation-in-part of Ser. No. 09/361,532 which was filed on Jul. 27, 1999 now U.S. Pat. No. 6,261,242 entitled Biopsy Sampler and is assigned to the same assignee as the present invention.

BACKGROUND

1. Field of the Invention

This invention relates to biopsy sampling.

2. Description of Related Art

There are many biopsy procedures in which tissue samples are taken for later histology. In "cold" biopsy procedures, surgical forceps are inserted within, for example, an endoscope, and are used to resect (i.e., cut) a tissue sample from, for instance, the biliary tree or colon. The forceps, and, hence, the tissue sample, are then removed from the patient through the endoscope.

Extensive bleeding can occur as a result of cold resecting, which can lead to dangerous blood loss levels. Hence, after the tissue sample is removed, another device can be inserted into the patient through the endoscope to stop the bleeding. These devices include tamponade devices which apply pressure to the bleeding site to stop the bleeding, devices which apply alcohol to the bleeding site to stop the bleeding, and electro-cautery devices which apply radio frequency (RF) energy to one or more electrodes (monopolar or bipolar) in contact with the bleeding site to cauterize the tissue and stop the bleeding. Following resecting, time is required to remove the forceps and tissue sample and insert a device to stop the bleeding. During this time, the resecting site continues to bleed.

Alternatively, a "hot" biopsy procedure is performed using surgical forceps in which the jaws are electrodes (bipolar or monopolar). After the tissue sample is resected, the forceps are brought in contact with tissue remaining at the resecting site and RF energy is applied to the forceps to cause current to flow (i.e., cauterization) through the resecting site tissue to coagulate the tissue and stop the bleeding. Coagulation of the tissue may also kill cancerous or precancerous tissue at the resecting site. Often, RF energy is applied to the forceps during resecting to help cut the tissue sample as well.

The tissue sample is again removed from the patient through the endoscope for histology. The tissue sample, however, may be inadvertently cauterized when the resecting site is cauterized rendering the tissue sample unusable for histology, e.g., the question of cell malignancy cannot be answered. The forceps may be lined with insulating material to electrically isolate the tissue sample from the forceps. However, heat generated when the resecting site tissue is cauterized may coagulate the tissue sample within the forceps, again, rendering the tissue sample unusable for histology.

U.S. Pat. No. 5,336,222 to Durgin, Jr. et al., issued on Aug. 9, 1994 entitled Integrated Catheter For Diverse In Situ Tissue Therapy; U.S. Pat. No. 5,403,311 to Abele et al., issued Apr. 4, 1995 entitled Electro-Coagulation And Ablation And Other Electrotherapeutic Treatments Of Body Tissue, and U.S. Pat. No. 5,522,815, issued Jun. 4, 1996 to Durgin, Jr., et al. and entitled Integrated Catheter For Diverse In Situ Tissue Therapy are assigned to the assignee of the present application and are hereby incorporated herein in their entirety by reference.

SUMMARY

In one aspect, the invention features an assembly for taking a biopsy sample from a site within the body of a patient. The assembly includes a resecting device having a cutter near its distal end for resecting and containing a tissue sample and a sheath exterior to the resecting device and sized to be present within the body with the resecting device. The sheath includes an electrode element electrically isolated from the resecting device and disposed on the sheath's outer surface for cauterizing tissue. The resecting device and the sheath cooperate to permit sequential resecting of a tissue sample from a resecting site and cauterizing of the site with the cutter sufficiently spaced from the electrode element to avoid heat damage to the tissue sample.

Implementations of the invention may include the following features. The sheath may include a lumen sized to slidably receive the resecting device or the sheath and the resecting device may be constructed as a unitary device where the cutter extends distally of the termination of the sheath and the electrode is spaced proximally of the cutter. The cutter may include forceps. The electrode element may be a monopolar electrode or a pair of bipolar electrodes, and, in both cases, the electrodes may be cylindrical. The bipolar electrodes may also be "C" shaped. Additionally, the sheath may be precurved or the sheath may be deflectable through the use of a tension wire having a distal end fixed toward the distal end of the sheath such that pulling on a proximal end of the tension wire causes a distal portion of the sheath to bend. The sheath may include a lumen disposed in its sidewall for receiving an electrical connection to the electrode element, and the same lumen can be used for receiving the tension wire. The assembly can be sized to pass through an endoscope.

In another aspect, the invention features an assembly for taking a biopsy sample from a site within the body of a patient. The assembly includes a resecting device including forceps near its distal end for resecting and containing a tissue sample, and a sheath exterior to the resecting device and sized to be present within the body with the resecting device. The sheath includes a lumen sized to slidably receive the resecting device and an electrode element electrically isolated from the resecting device and disposed on the sheath's outer surface for cauterizing tissue. The resecting device and the sheath are cooperatively constructed to permit sequential resecting of a tissue sample from a resecting site and cauterizing of the site with the forceps spaced from the electrode element sufficiently to avoid heat damage to the sample.

In another aspect, the invention features an assembly for taking a biopsy sample from a site within the body of a patient. The assembly includes a resecting device including forceps near its distal end for resecting and containing a tissue sample, and a sheath exterior to the resecting device and sized to be present within the body with the resecting device. The sheath and the resecting device are constructed as a unitary device and the forceps extend distally of the termination of the sheath. The sheath includes an electrode element electrically isolated from the resecting device, spaced proximally to the forceps, and disposed on the sheath's outer surface for cauterizing tissue. The resecting device and the sheath are cooperatively constructed to permit sequential resecting of a tissue sample from a resecting site and cauterizing of the site with the forceps spaced from the electrode element sufficiently to avoid heat damage to the sample.

In another aspect, the invention features a method for taking a biopsy sample with an assembly from a site within the body of a patient. The assembly includes a resecting device having a cutter near its distal end for resecting and containing a tissue sample and a sheath exterior to the resecting device and sized to be present within the body with the resecting device. The sheath includes an electrode element electrically isolated from the resecting device and disposed on the sheath's outer surface for cauterizing tissue. The resecting device and the sheath cooperate to permit sequential resecting of a tissue sample from a resecting site and cauterizing of the site with the cutter sufficiently spaced from the electrode element to avoid heat damage to the tissue sample. The method further includes resecting a tissue sample from a resecting site with the resecting device and containing the tissue sample with the cutter. Additionally, the electrode element is located at the resecting site with the cutter containing the sample spaced from the electrode element, and the site is cauterized by application of power to the electrode element.

Implementations of the invention may include the following features. The sheath may include a lumen sized to slidably receive the resecting device, and the method may further include inserting the resecting device within the lumen of the sheath, extending the resecting device from a distal end of the sheath to position the resecting device at a resecting site, and withdrawing the resecting device within the lumen a distance away from the distal end of the sheath. The method may include extending the cutter from the sheath to space the cutter from the electrode. The method may also include withdrawing the resecting device completely from the sheath, removing the tissue sample from the resecting device, reinserting the resecting device within the lumen of the sheath, extending the resecting device from the distal end of the sheath to position the resecting device at a new resecting site, resecting a tissue sample from the new resecting site with the resecting device, containing the tissue sample with the cutter, withdrawing the resecting device within the lumen a distance away from the electrode element, positioning electrode element at new resecting site, and cauterizing the new resecting site by application of power to the electrode element. The method may also include inserting an endoscope within the body and inserting the sheath within the endoscope. Moreover, the sheath and the resecting device may be constructed as a unitary device where the cutter extends distally of the termination of the sheath and the electrode is spaced proximally of the cutter, and the method may further include positioning the resecting device and the sheath along a treatment path, positioning the resecting device at a resecting site, resecting a tissue sample from the resecting site with the resecting device, containing the tissue sample with the cutter, positioning the electrodes at the resecting site, and cauterizing the site by application of power to the electrode element.

Embodiments may include one or more of the following advantages: For example, polyps and other aberrant tissue can be resected and the resection site can be cauterized without heat-damaging the sample or removing the sampling device from the patient's body before cauterizing. For example, in embodiments, the resected tissue is slid axially a predetermined short distance away from the cauterizing electrodes so that heat from the electrodes does not affect the sample integrity. The bleeding of the resecting site is quickly electro-cauterized. The resection can be carried out using a cauterizing sheath having electro-cautery electrodes disposed on a distal end of the sheath and having surgical forceps slidably disposed within a lumen in the sheath. The surgical forceps are used to resect the tissue sample and axially remove the sample from the resecting site, while the electro-cautery electrodes are used to cauterize the resecting site to stop bleeding. In other embodiments, the distance between the electrodes and the forceps is fitted at a preselected spacing sufficient to avoid heat damage when the assembly is maneuvered to position the electrodes at the resection site for cauterization. The need for additional tissue removal, additional biopsy procedures, complications from blood loss, time in surgery, and patient trauma may all be reduced. The instrument can be constructed for use with a variety of existing surgical devices and can be easily manufactured.

In each of these embodiments of the invention the electrode element may reside on the outer sheath of the assembly, the distal end of the assembly or both. Various configurations of electrode elements are possible including parallel horizontal configuration or an alternating spiral configuration. In addition, electrode elements may include a three dimensional configuration to aid in cauterization.

Additional advantages and features are apparent from the following.

DETAILED DESCRIPTION

FIG. 7b is an end view of the assembly of FIG. 7a;

Figure 9A:
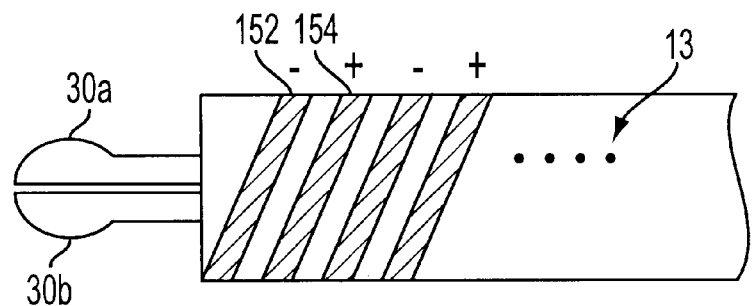
Figure 9B:
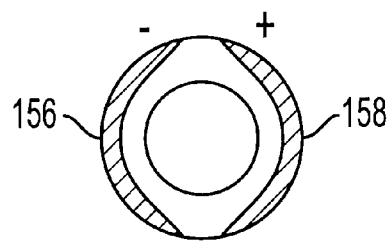
Figure 9C:
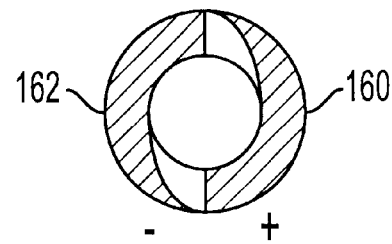
Figure 10C:
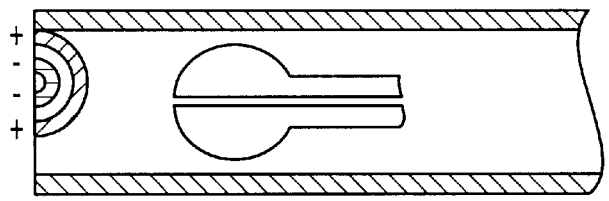
Figure 10D:
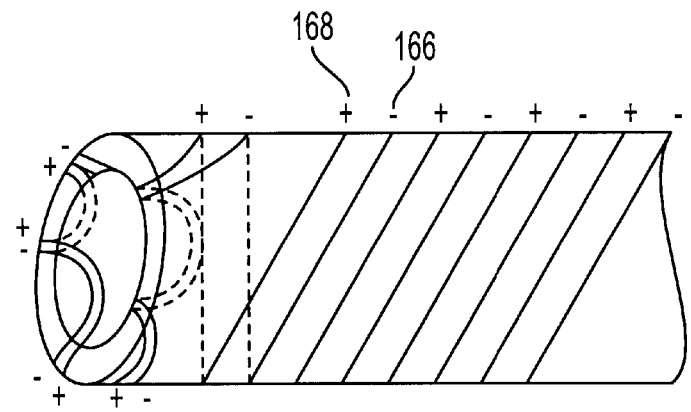
Figure 10E:
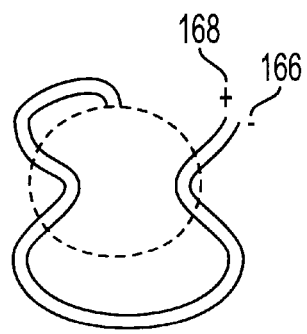
Figure 18A:
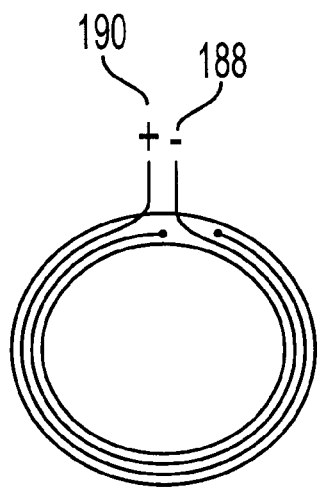
Figure 18B:
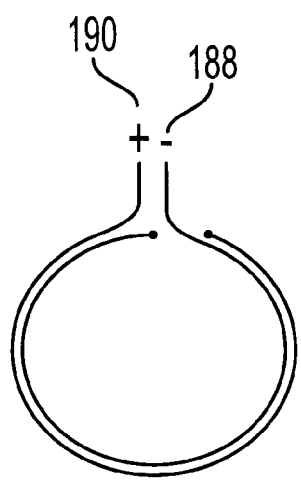

FIGS. 9a, and 9b–9c are side and two end views illustrating an embodiment of the spiraling electrodes of the present invention;

FIGS. 10a and 10b are side and end views illustrating another embodiment of the spiraling electrodes of the present invention;

FIG. 10c is a side view illustrating a configuration for connecting the spiraling electrodes of FIG. 10a cutaway;

FIG. 10d is a axiomatic view of the embodiment of FIGS. 10a, 10b and 10c;

FIG. 10e illustrates how the parallel electrodes of the embodiment displayed in FIGS. 10a and 10b may be situated around the distal end of the sheath to allow bipolar contacts;

FIGS. 11a, and 11b are side and end views illustrating another embodiment of the spiraling electrodes of the present invention;

FIGS. 12a, and 12b are a side view and an end view illustrating another embodiment of the spiraling electrodes of the present invention;

FIGS. 13a, and 13b are side and end views illustrating another embodiment of the spiraling electrodes of the present invention;

FIGS. 14–17 are side views illustrating various configurations of the electrodes; and FIGS. 18a and 18b are two end views of another embodiment of the present invention.

DESCRIPTION OF ILLUSTRATED EMBODIMENTS

Referring to FIGS. 1a, 1b, 2, and 3, a biopsy assembly 10 includes a cauterizing sheath 12 and a resecting device 14. Sheath 12 includes a working lumen 16 extending from a proximal end 18 to a distal end 20 defined by an inner lumen wall 17 and sized to receive resecting device 14. The sheath also includes a pair of bipolar electrodes 22a, 22b mounted on an outer sheath surface 13 near distal end 20. Sheath 12 also includes an electrical connector 24, for connection to a radio frequency (RF) generator (not shown), and a lumen 26, extending between outer surface 13 and inner surface 17 of sheath 12 from electrical connector 24 to electrodes 22a, 22b. Two wires 28 are disposed within lumen 26, and each wire 28 electrically connects one of the electrodes 22a and 22b to electrical connector 24. Wires 28 are each coated with a layer of electrical insulation to prevent electrical contact between the wires.

Resecting device 14 is slidably positioned within working lumen 16 and includes a cutter, for example, forceps 30 (e.g., cup-shaped jaws, 30a, 30b), a handle 32, and a jacket 33. Handle 32 includes a positioning ring 35 and a forceps grip 38. Positioning ring 35 is mechanically coupled to forceps 30 through wires 31 and forceps grip 38 is mechanically coupled to forceps 30 through jacket 33. Positioning ring 35 or jacket 33 is pulled (arrow 34, FIG. 2) to axially withdraw forceps 30 within working lumen 16 toward proximal end 18 of sheath 12 and pushed (arrow 36, FIG. 3) to axially extend forceps 30 from working lumen 24 at distal end 20 of sheath 12. Once extended from working lumen 24, forceps grip 38 is pushed (arrow 36) to open (dashed lines 42a, 42b, FIGS. 1b, 3) and pulled (arrow 41) to close (solid lines 44a, 44b, FIGS. 1b, 2, 3) jaws 30a and 30b of forceps 30. Because electrodes 22a and 22b are disposed on outer sheath surface 13 and wires 28 are positioned within electrical lumen 26, forceps 30 are electrically isolated from electrodes 22a and 22b.

Handle 32 is used to extend forceps 30 from working lumen 16 beyond distal end 20 of sheath 12 and is used to open jaws 30a and 30b to surround a tissue sample, e.g., a polyp, and close jaws 30a and 30b to resect and contain the polyp. Handle 32 is then used to withdraw forceps 30 within working lumen 16 to spatially remove forceps 30, and, hence, the tissue sample, from electrodes 22a, 22b on distal end 20 of sheath 12. Proximal end 18 of sheath 12 is then pushed to locate electrodes 22a, 22b adjacent tissue remaining at the resecting site and RF energy is applied to electrodes 22a, 22b, through electrical connector 24 and wires 28, to electro-cauterize the tissue remaining at the resecting site.

In a particular embodiment, sheath 12 is teflon, which has a low coefficient of friction allowing resection assembly 12, including stainless steel forceps 30, stainless steel coil jacket 33, and stainless steel wires 27 to easily slide within working lumen 16 and a relatively high melting point to prevent sheath 12 from melting when tissue adjacent to electrodes 22a, 22b is heated during cauterization. Sheath 12 has a wall thickness of approximately 0.15 mm and is about 150 cm in length. In one embodiment, the outer diameter of sheath 12 is about 2.6 mm, the diameter of working lumen 16 is approximately 2.3 mm, and the closed diameter of the jaws of forceps 30 is approximately 2.2 mm which provides about 0.1 mm of clearance between forceps 30 and inner sheath surface 17 when the jaws of forceps 30 are closed and withdrawn within working lumen 16. Such an assembly can be passed through a lumen (i.e., lumen 54, FIG. 4a) in an endoscope (i.e., endoscope 50, FIG. 4a) having a diameter of about 2.7 mm. Electrodes 22a and 22b are cylindrical electrodes having a width, W1, of approximately 2.0 mm and are separated along outer sheath surface 13 by a distance, d1, of about 4.0 mm. After forceps 30 have resected and are containing a tissue sample, forceps 30 are withdrawn (arrow 34, FIG. 2) within working lumen 16 a distance d2 of approximately 2 inches or more from electrode 22b to prevent the tissue sample from being damaged by cauterization or by heat generated during tissue coagulation.

In another embodiment, the outer diameter of shaft 12 is again 2.6 mm and the diameter of working lumen 16 is again approximately 2.3 mm, however, the closed diameter of the jaws of forceps 30 is approximately 1.8 mm. In yet another embodiment, the outer diameter of shaft 12 is about 3.7 mm, the diameter of working lumen 16 is approximately 3.4 mm and the closed diameter of the jaws of forceps 30 is approximately 3.3 mm.

1. Use

Referring to FIGS. 4a–4f, the operation of assembly 10 will be described with regard to the removal of a polyp 46 from a patient's colon 48. The patient is prepared by inserting an endoscope 50 to the region of treatment. The physician, with optical lens 52, inspects the region. Through a lumen 54 in endoscope 50, the region is flushed, e.g., with saline. Outside the body, the resecting device is inserted within the sheath such that the forceps are near but do not extend from the distal end of the sheath.

Figure 1:
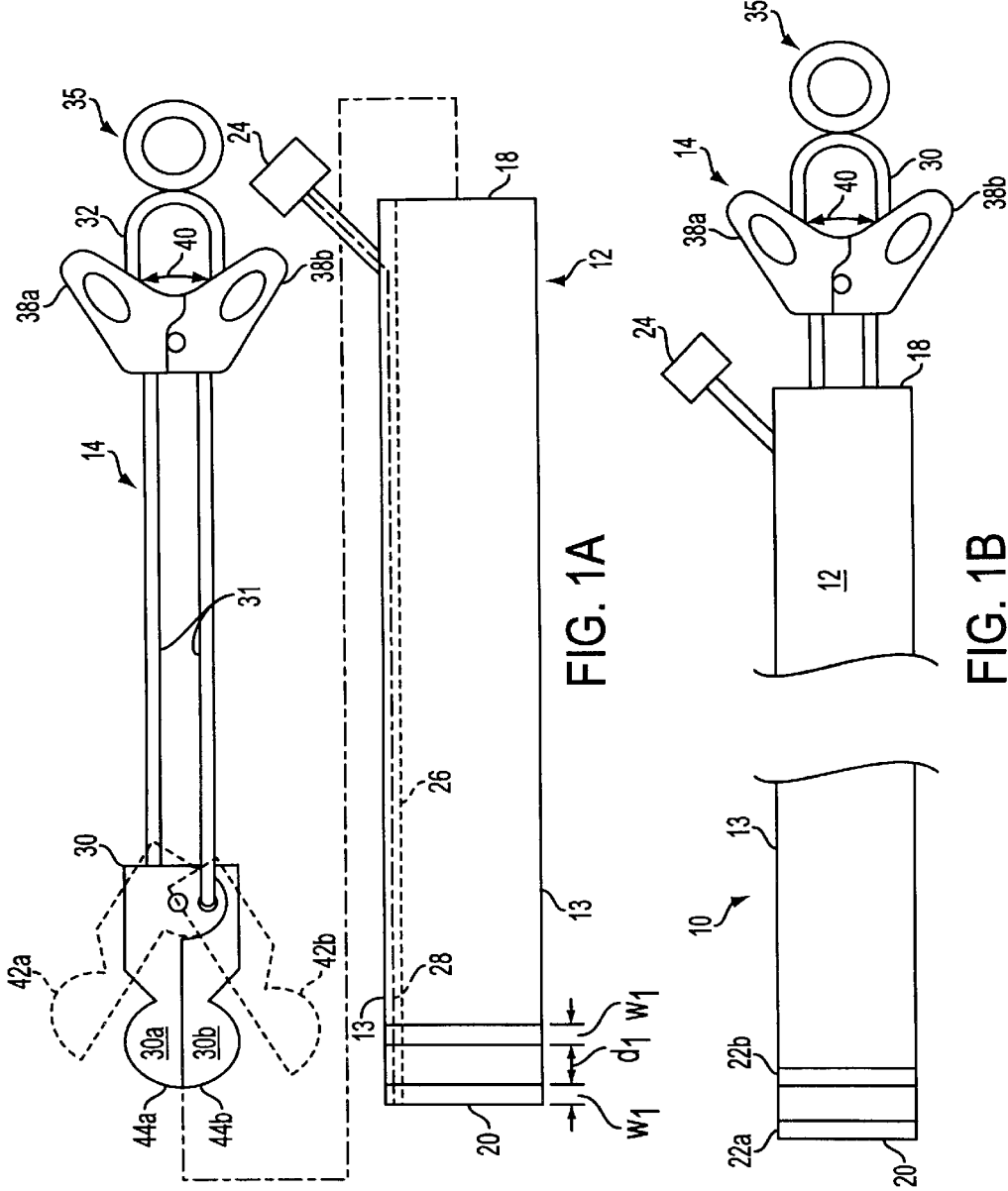
FIG. 1a is an exploded side view of a biopsy assembly including a resecting device and a cauterizing sheath.
FIG. 1b is view similar to FIG. 1a with the resecting device positioned within the cauterizing sheath.
Figure 2:
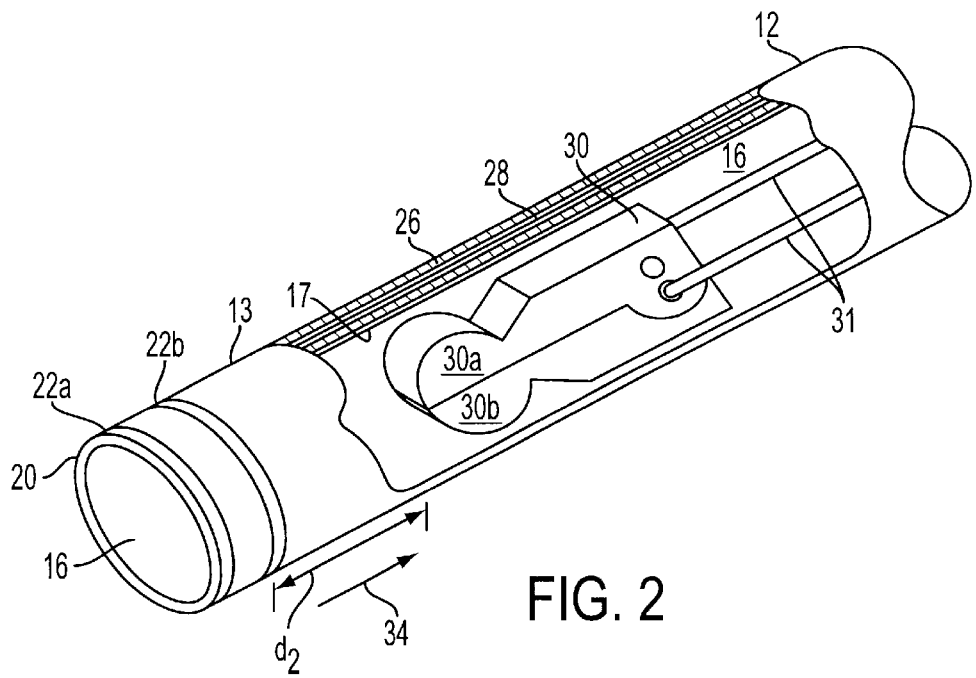
FIG. 2 is an enlarged perspective view of a distal portion of the biopsy assembly of FIG. 1b, with a part of the sheath cut-away.
Figure 3:
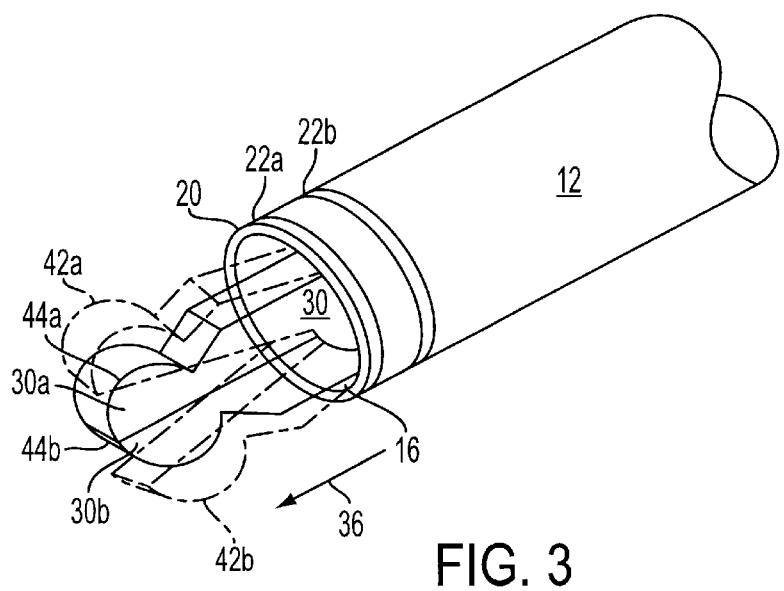
FIG. 3 is an enlarged perspective view of a distal portion of the biopsy assembly of FIG. 1b with surgical forceps of the resecting device axially extended from the cauterizing sheath.
Figure 4A:
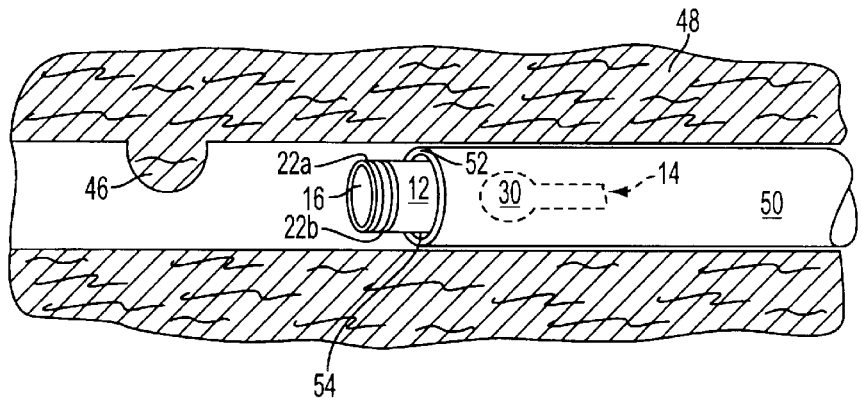
FIGS. 4a–4c and 4f are side views of the distal portion of the biopsy assembly of FIG. 1b disposed within an endoscope and in use within a colon.

Referring particularly to FIG. 4a, sheath 12 and resecting device 14 are then inserted together in lumen 54 of endoscope 50. Resecting device 14 provides additional strength to sheath 12 to prevent sheath 12 from buckling as it is inserted within endoscope 50. Alternatively, biopsy assembly 10 can be inserted within endoscope 50 before endoscope 50 is inserted within the patient to save time in surgery.

Figure 4B:
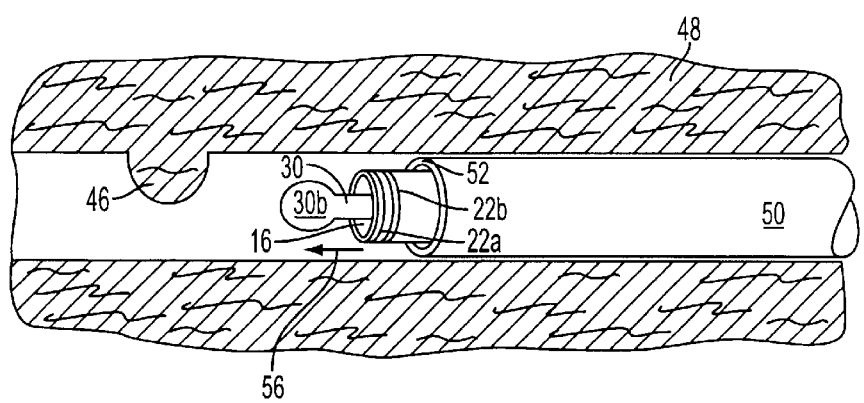
Figure 4C:
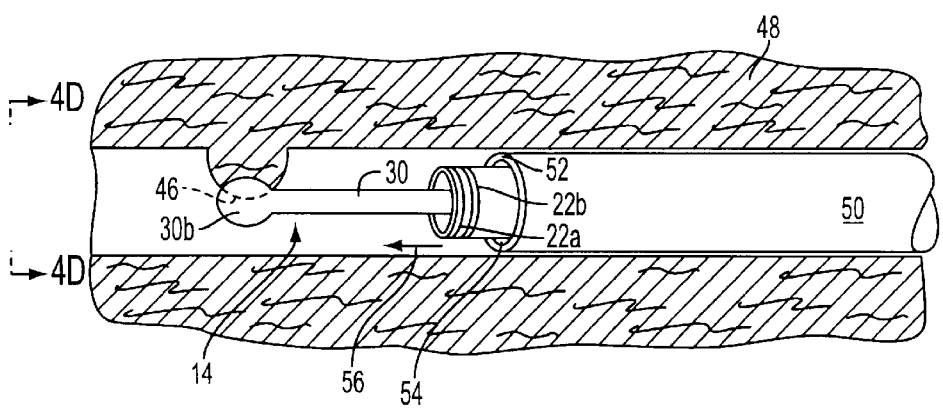
Figure 4D:
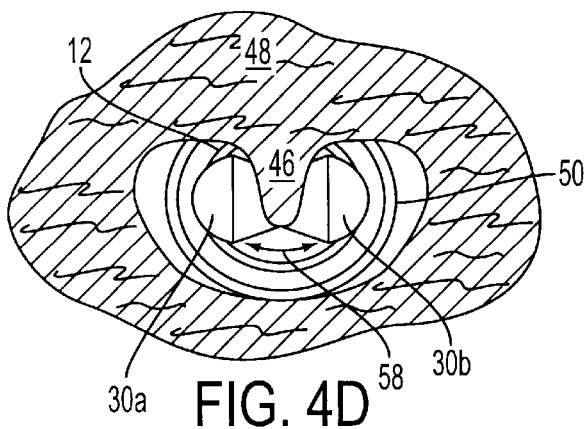
FIGS. 4d and 4e are end views of the distal end of the biopsy assembly of FIG. 1b disposed within an endoscope and in use within a colon.
Figure 4E:
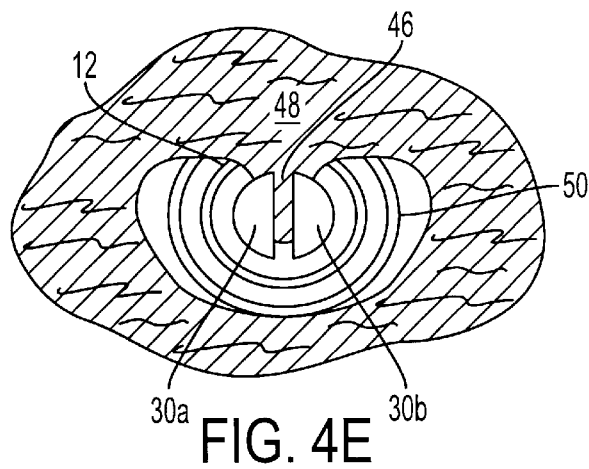

Referring to FIG. 4b, once positioned, resecting device 14, including forceps 30, is extended (arrow 56) beyond distal end 20 of sheath 12, and, jaws 30a, 30b are opened (arrow 58, FIGS. 4c and 4d). As resecting device 14 is further extended, jaws 30a and 30b surround polyp 46. The jaws are closed (FIG. 4e) causing the edges of jaws 30a and 30b to resect polyp 46 or a portion of polyp 46.

Figure 4F:
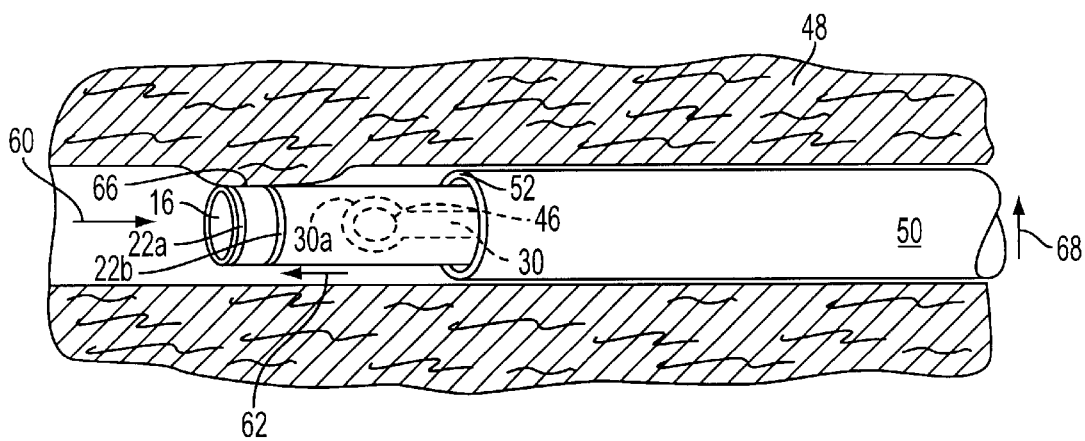

Referring to FIG. 4f, resecting device 14, including forceps 30 containing polyp 46, is then withdrawn (arrow 60) within working lumen 16 of sheath 12 approximately 2 inches or more proximal to electrode 22b. Sheath 12 is pushed forward (arrow 62) and endoscope 50 is pushed up (arrow 64) to bring electrodes 22a, 22b in contact with resecting site 66. RF energy is then applied to electrodes 22a, 22b through wires 28 (FIG. 1b) and electrical connector 24 to cause current to pass through the resecting site tissue between electrodes 22a, 22b. The current heats the resecting site to approximately 60–100 degree C. which is sufficient to coagulate the resecting site tissue. The distance between forceps 30 and electrodes 22a, 22b is sufficient to prevent current from traveling through polyp 46 within forceps 30 and sufficient to prevent the heat in the resecting site from coagulating polyp 46 within forceps 30. An irrigant flush, e.g., saline, through working channel 16 can also be used to cool forceps 30 to provide additional protection against coagulation of polyp 46 within forceps 30. As a result, an undamaged tissue sample is taken and the resecting site is quickly cauterized to prevent damaging blood loss.

Endoscope 50, sheath 12, and resecting device 14 may then be removed from the patient and polyp 46 recovered from forceps 30 for histology. Alternatively, only resecting device 14 is removed, through sheath 12 and endoscope 50, from the patient so that polyp 46 can be recovered for histology, and resecting device 14 is then reinserted within sheath 12 and endoscope 50 for removal of another tissue sample.

2. Other Embodiments

A single cylindrical monopolar electrode can be disposed on the outer sheath surface at the distal end of the sheath. With a monopolar electrode, the patient is placed on a grounding plate, and when RF energy is applied to the electrode, current travels between the electrode and the grounding plate. The current is concentrated in tissue adjacent to the electrode and causes sufficient heat to coagulate the adjacent tissue.

Figure 5:
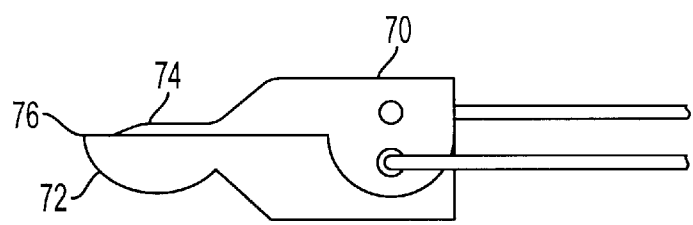
FIG. 5 is a side view of another embodiment of an assembly.

Referring to FIG. 5, forceps 70 can be provided having one cup-shaped jaw 72 and one flat jaw 74, where the flat jaw 74 is sharp along a forward edge 76 and is used to resect tissue that is then caught and contained by cup-shaped jaw 72. Forceps 70 or forceps 30 (FIG. 1a) can also include a needle (not shown) to assist in resecting tissue samples.

Figure 6:
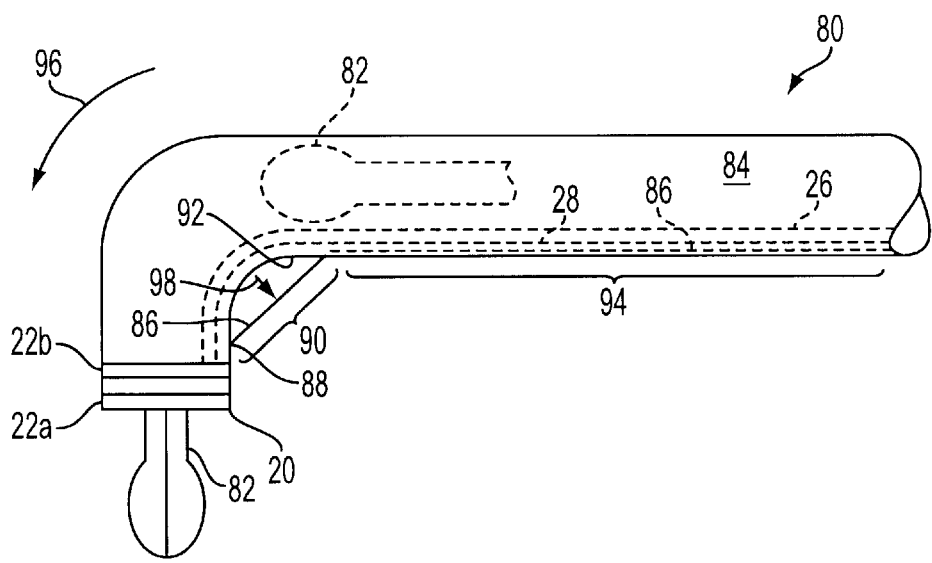
FIGS. 6 and 7a are side views of other embodiments of an assembly.

Referring to FIG. 6, a deflectable sheath 80 includes a resecting assembly 82 slidably disposed within an cauterizing sheath 84. Resecting assembly 82 is similar to resecting assembly 12 described above with respect to FIGS. 1a and 1b, and sheath 84 is similar to sheath 12 described above, except that sheath 84 includes a tension wire 86 for bending distal end 20 of sheath 84. A distal end 88 of tension wire 86 is fixed to sheath 84. A portion 90 of tension wire 86 extends along an outer surface 92 of sheath 84 and a proximal portion 94 of tension wire 86 extends within electrical lumen 26 of sheath 84. The electrical insulation coating each of the wires 28 prevents electrical contact between tension wire 86 and wires 28.

After positioning sheath 84 and extending resecting assembly 82 beyond a distal end of sheath 84, the physician pulls a proximal end (not shown) of tension wire 86. Because distal end 88 is fixed to sheath 84, pulling on wire 86 causes sheath 84 (and flexible jacket 33, FIG. 1a) to bend (arrow 96) and lifts (arrow 98) wire 86 off outer surface 92 of sheath 84. Bending the distal end of sheath 84 allows the physician greater flexibility in removing tissue samples and cauterizing resecting site tissue. Alternatively, sheath 12 (FIGS. 1a, 1b) can be manufactured to be precurved.

Figure 7A:
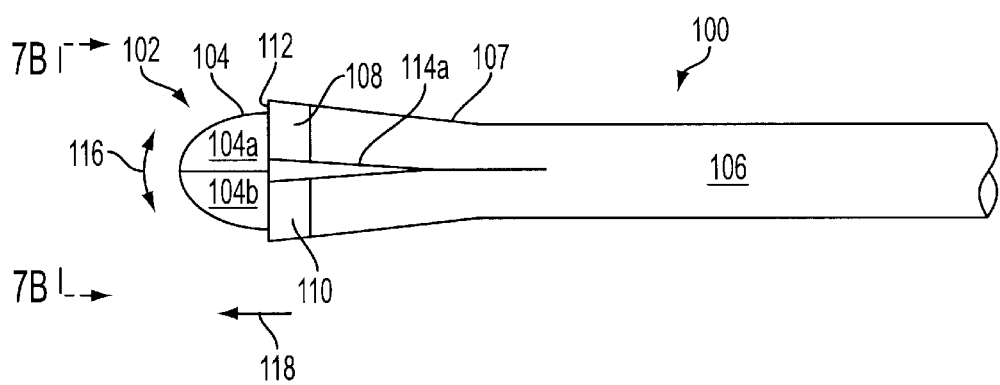
Figure 7B:
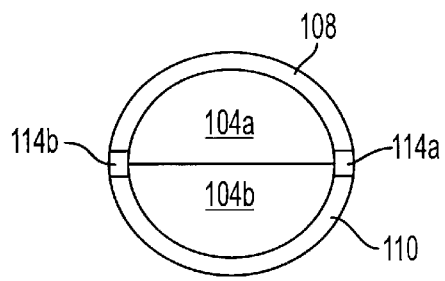

Referring to FIGS. 7a and 7b, a biopsy assembly 100 includes a resecting device 102 including forceps 104 (having jaws 104a and 104b) slidably disposed within cauterizing sheath 106. "C" shaped electrodes 108, 110 are disposed on an outer surface 107 and a distal end 112 of sheath 106 and are separated by elastic members 114a, 114b. The closed diameter of the jaws of forceps 104 is, for example, 3.3 mm, which is larger than the diameter, for example, 3.0 mm, of a lumen (not shown) of sheath 106. Hence, inserting a proximal end of resecting device 102 in distal end 112 of the lumen of sheath 106, eventually pushed forceps 104 against distal end 112 and forces elastic members 114a, 114b to expand (arrow 116).

Biopsy assembly 100 is then inserted within an endoscope and positioned within a patient. Once in position, resecting device 102 is extended (arrow 118) from distal end 112 of sheath 106 and elastic member 114 compresses leaving "C" shaped electrodes 108, 110 separated by a distance of approximately 0.2 mm. Forceps 104 are used to resect a tissue sample from a resecting site, and electrodes 108 and 110 are then brought in contact with the resecting site tissue. Before RF energy is applied to electrodes 108 and 110 to cauterize the resecting site tissue, resecting device 102 is further extended (arrow 118) a predetermined distance (e.g., 2 inches or more) away from distal end 112 of sheath 106. Both sheath 106 and resecting device 102 are then removed together from the endoscope in order to retrieve the tissue sample.

Cylindrical electrodes 22a and 22b (FIG. 1a) can be replaced with two "C" shaped electrodes disposed on distal end 20 of sheath 12 and separated by a fixed distance, e.g., 0.2 mm. With such an arrangement, forceps 30 can be pulled within sheath 12, the distal end of the sheath can be pushed against a resecting site, for example, at a bend or elbow in a colon, and RF energy can be applied to the electrodes to cauterize the resecting site tissue.

Figure 8A:
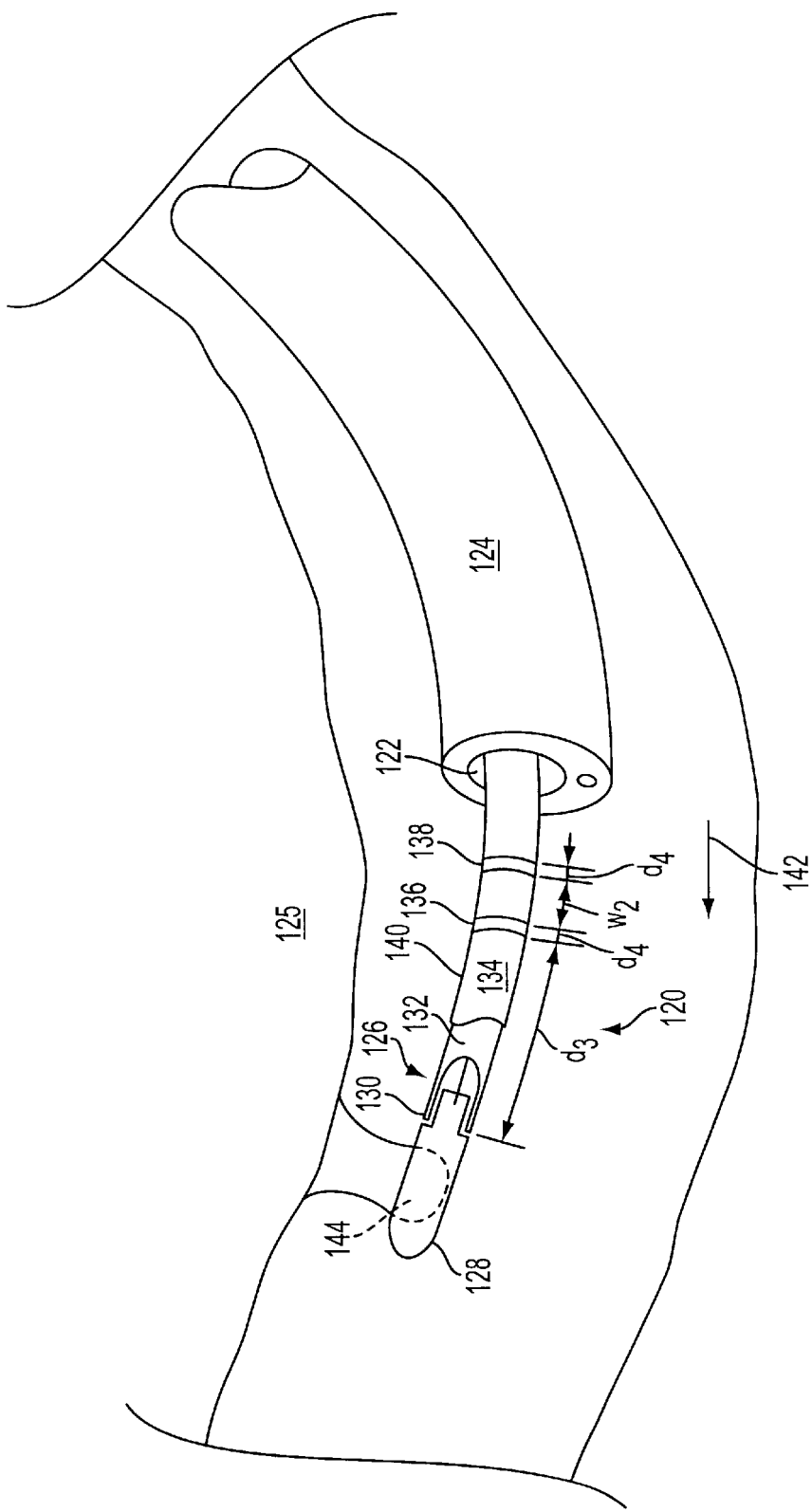
FIGS. 8a and 8b are side views illustrating structure and use of another embodiment of an assembly, with a portion of the assembly of FIG. 8a cut-away.
Figure 8B:
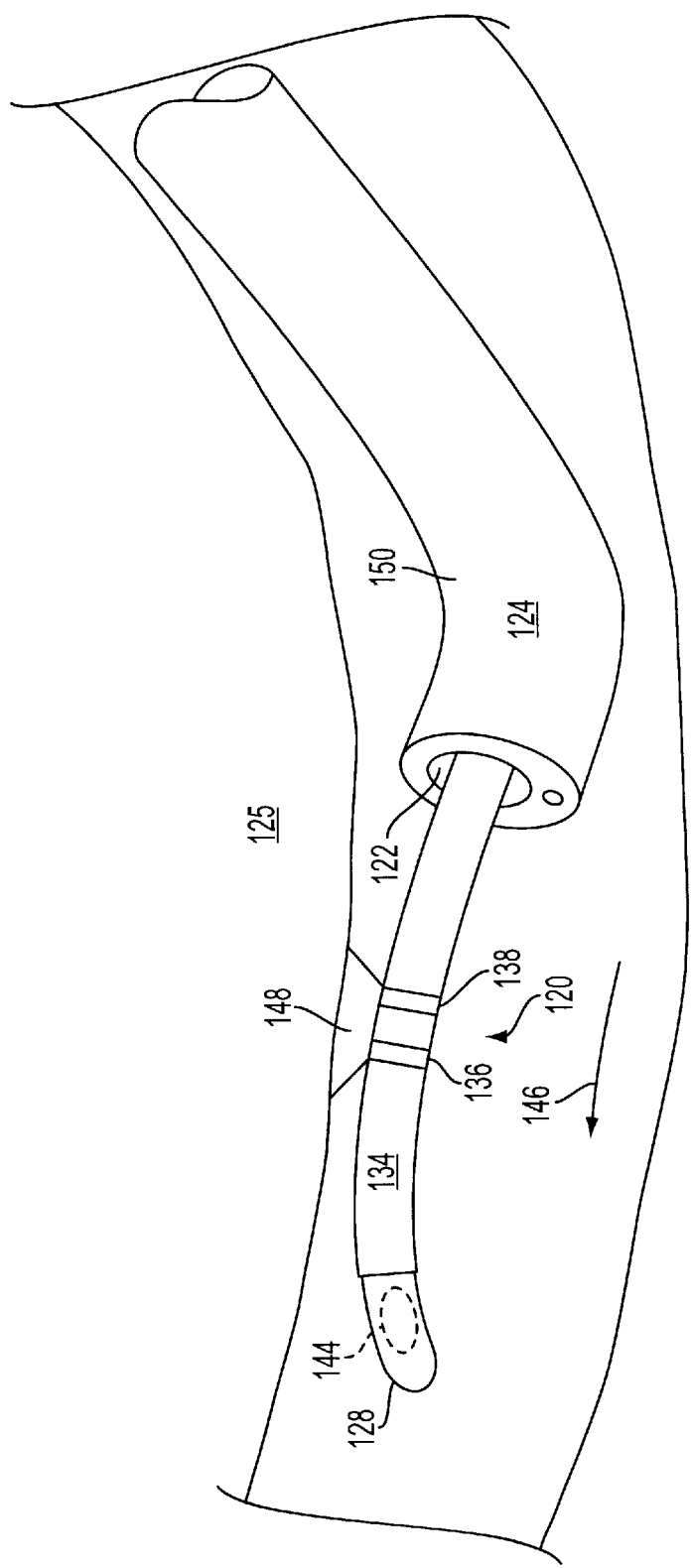

Referring to FIGS. 8a and 8b, a biopsy assembly 120 is shown inserted within a lumen 122 of a deflectable endoscope 124 which is positioned within a colon 125 of a patient. Biopsy assembly 120 includes a resecting device 126 having forceps 128 disposed on a distal end 130 of a stainless steel coil 132. A teflon shaft 134 is disposed on stainless steel coil 132, and two cylindrical electrodes 136, 138 are disposed on an outer surface 140 of shaft 134. Shaft 134 electrically isolates forceps 128 from electrodes 136, 138. Shaft 134 is extended (arrow 142, FIG. 8a) through endoscope lumen 122 and the jaws of forceps 128 are opened. Shaft 134 is then further extended to position the opened jaws of forceps 128 around polyp 144. The jaws are then closed to resect polyp 144 and to contain polyp 144. Shaft 134 is then further extended (arrow 146, FIG. 8b) to bring electrodes 136 and 138 toward resecting site 148. Deflectable endoscope 124 is then bent 150 to bring electrodes 136 and 138 in contact with resecting site 148, and RF energy is applied to the electrodes to cauterize tissue at the resecting site 148.

Shaft 134 has a wall thickness of approximately 0.2 mm and is about 150 cm in length. The closed diameter of forceps 128 is about 2.2 mm. The outside diameter of stainless steel coil 132, and, hence, the inside diameter of shaft 134, is also about 2.2 mm. The outside diameter of shaft 134 is about 2.6 mm, and the diameter of endoscope lumen 122 is about 2.7 mm which provides about 0.1 mm of clearance between shaft 34 and the surface of lumen 122. Electrode 136 is separated by a distance, d3, of approximately 2 inches from forceps 128 to prevent tissue samples contained in forceps 128 from being damaged by cauterization or by heat from coagulation. Electrodes 136 and 138 are cylindrical electrodes having a width, W2, of approximately 2.0 mm and are separated by a distance, d4, of about 4.0 mm.

Alternate embodiments of the electrode configuration (22a & 22b of FIG. 1b, and 136 & 138 of FIG. 8b) are also possible and included within the present invention. FIG. 9a shows alternating spiral electrodes 152, 154 which may be included on the outer sheath surface 13. The alternating spiral electrodes 152, 154 use RF energy from electrical connector 24 (FIG. 1b) to establish a catherization field between the electrodes of differing polarity. Wires 28 carry the RF energy from electrical connector 24 to spiral electrodes 152, 154. FIGS. 9b and 9c show alternative electrode placement on the distal end 20 of the catheter sheath. FIG. 9b shows the inclusion of bipolar electrodes 156, 158 on distal end 20 of the sheath which is an extension of the spiral pattern included on the circumference of the sheath. Alternatively, FIG. 9c shows a pattern for electrodes 160, 162 in which distal end 20 of the sheath is divided into approximately two even areas for which electrodes of differing polarity are attached. One of ordinary skill in the art would understand that the spiral electrodes 152, 154 may extend long any length of outer sheath surface 13.

FIGS. 10a and b show an alternate arrangement of the electrode configuration on outer sheath surface 13 and distal end 20 of the sheath. In FIG. 10a the electrodes are applied to outer sheath surface 13 and include a tapered design which allows the spacing 164 between the electrodes to be reduced near the distal end 20. By reducing the spacing 164 between the electrodes 166, 168 in FIG. 10a, the electrode placement on the end of the sheath may also be modified as shown in FIG. 10b. FIG. 10b includes multiple electrode pairs which have been placed on distal end 20. The inclusion of the multiple electrode pairs allows cauterization with greater precision. Additionally, the addition of the electrode pairs on the end of the sheath allows the physician direct visualization as the end of the catheter is used to cauterize the bleeding tissue. The electrodes included on distal end 20 may be effected by either connecting to electrodes 166 and 168 or by partially running electrodes into the distal end 20 of the sheath body. FIG. 10c shows how branches can be used to interconnect individual electrodes at distal end 20. FIG. 10d further illustrates the embodiment of FIGS. 10a–c, but in axiometric view to more clearly exhibit a manner in which the electrodes may continuously extend around the distal end of the sheath and allow for bipolar point contacts. FIG. 10d illustrates the connections between the electrodes 168 and 166 on the sheath surface and the electrode pairs on the distal end 20. FIG. 10e further illustrates the embodiment of FIGS. 10a–10d. However, FIG. 10e illustrates how the parallel electrodes may be situated around the distal end of the sheath to allow for bipolar contacts. In FIG. 10e, the electrodes are portrayed in a plane perpendicular to the axis of the sheath. The electrodes in FIG. 10e would be folded down to the inner and outer surfaces of the sheath to create the embodiments of FIGS. 10a–10d.

FIGS. 11a and b show another configuration for the electrodes 170, 172 on the sides of the sheath and on the sheath ends. FIG. 11a shows electrodes 170, 172 which run from the proximal end 18 of the catheter to distal end 20 in parallel. As seem in FIG. 11b these parallel electrodes are continued on the end of the sheath. Electrode pairs 170, 172 are insulated along portions of the sheath where cauterization is not desired and to protect tissue samples from inadvertent cauterization.

FIGS. 12a–12b show another embodiment of the present invention in which the positive electrodes 174 are run along the outer sheath surface 13 and the negative electrodes 176 along the inner sheath surface 17. In FIG. 12a positive electrodes 174 are positioned along outer sheath surface 13 and negative electrodes 176 are positioned along the inner sheath surface 17. Electrodes 174 and 176 are electrically insulated from one another in areas in which cauterization is undesired. FIG. 12b shows distal end 20 of this embodiment. One of ordinary skill would understand that the position of the electrodes in this configuration can be switched so that positive electrodes 174 are on the inner sheath surface 17 and negative electrodes 176 are on the outer sheath surface 13. FIG. 12b illustrates the electrode arrangement which would then be fitted to the distal end 20 of the sheath, by bending the electrodes around the inner and outer surfaces and adhering them to the sheath, or by alternative placement methods. While FIGS. 12a and 12b show the positive electrode on the outside of the sheath and the negative electrode on the inside, one of ordinary skill in the art would understand both elements can be on the outside, on the inside or divided between the inside and outside of the sheath.

FIGS. 13a–13b show the number of electrodes on the distal end can be increased to more accurately cauterize a specific area. In this embodiment, each electrode is connected to electrical connector 24 by its own control wire 178.

FIGS. 14–17 show that the electrodes may be located at distal end 20 or on the outer sheath surface (sides) 20 of the sheath. Additionally, the electrodes may be shaped differently to affect cauterization to different areas. FIG. 14 shows electrodes 180 which are configured in the shape of raised circular areas or domes. FIG. 15 shows electrodes 182 which are configured as on one side of outer sheath surface 13. FIG. 16 shows electrodes 184 which are configured as pyramids. FIG. 17 shows electrodes 186 which are located only on distal end 20. One of ordinary skill in the art would understand that electrodes 180 and 184 may be located on distal end 20, outer sheath surface 13, or on both distal end 20 and outer sheath surface 13. Additionally, one of ordinary skill in the art would understand that the different shapes described here are not limiting and that the invention encompasses electrodes of various shapes including, but not limited to, squares, circles, triangles, rectangles. The electrodes, as shown by FIGS. 14 and 16 may also have a three dimensional shape to improve the contact between the tissue and the electrode.

FIGS. 18a and 18b illustrate a further embodiment of the invention. The positive 190 and negative 198 electrodes are brought to the distal end 20 of the sheath and wrapped parallel to each other in a plane perpendicular to the axis of the sheath. FIG. 18a illustrates the electrodes positioned on the distal end 20 of the sheath. FIG. 18b illustrates the same embodiment with the sheath removed for clarity of the illustration.

One of ordinary skill would understand that the electrode element may be placed on any medical device which is deployed through an endoscope. Such medical devices may be snares, biopsy samplers, scissors, baskets, blades, needles, knives, tomes, injection snares or any other medical devices used to perform tissue-plasty or surgical manipulation of tissue after which cauterization is desired.

Other embodiments are within the following claims.

What is claimed is:

1. An assembly for performing a medical procedure, comprising:
   an endoscopically deployed medical device for tissue-plasty, and
   a sheath exterior to said medical device and sized to be present within the body with said medical device, wherein said sheath and medical device are constructed as a unitary device, and wherein said medical device extends distally of the termination of said sheath,
   said sheath including an electrode element electrically isolated from said medical device, spaced proximally to said medical device, and disposed on said sheath's outer surface for cauterizing tissue,
   said medical device and sheath cooperatively constructed to permit sequential tissue-plasty and cauterization of tissue.

2. A method for performing a medical procedure, comprising:

including a medical device for tissue-plasty near its distal end, a sheath exterior to said medical device including an electrode element electrically isolated from said medical device, providing an assembly wherein said sheath and medical device are constructed as a unitary device wherein said medical device extends distally of the termination of said sheath and said electrode is spaced proximally of said medical device, positioning said medical device and said sheath along a treatment path, positioning said medical device at a tissue-plasty site, surgically manipulating said tissue-plasty site with said medical device; positioning said electrodes at said tissue-plasty site, and cauterizing said site by application of power to said electrode element.

3. An assembly for performing a medical procedure, comprising:

an endoscopically deployed medical device for tissue-plasty, and a sheath exterior to said medical device and sized to be present within the body with said medical device, said sheath including an electrode element electrically isolated from said medical device and disposed on said sheath's outer surface for cauterizing tissue, and said medical device and sheath being cooperatively constructed to permit spatial separation between said medical device and said electrode element, said medical device being constructed to surgically manipulate tissue prior to said cauterization; and wherein said outer sheath portion of said electrode element includes a spiral pattern.

4. An assembly for performing a medical procedure, comprising:

an endoscopically deployed medical device for tissue-plasty, and a sheath exterior to said medical device and sized to be present within the body with said medical device, said sheath including an electrode element electrically isolated from said medical device and disposed on said sheath's outer surface for cauterizing tissue, and said medical device and sheath being cooperatively constructed to permit spatial separation between said medical device and said electrode element, said medical device being constructed to surgically manipulate tissue prior to said cauterization; and wherein said outer sheath portion of said electrode element includes a parallel component of electrode element.

5. An assembly for performing a medical procedure, comprising:

an endoscopically deployed medical device for tissue-plasty, and a sheath exterior to said medical device and sized to be present within the body with said medical device, said sheath including an electrode element electrically isolated from said medical device and disposed on said sheath's outer surface for cauterizing tissue, and said medical device and sheath being cooperatively constructed to permit spatial separation between said medical device and said electrode element, said medical device being constructed to surgically manipulate tissue prior to said cauterization; and a "C" shaped portion of said electrode element located on a distal end of said outer sheath.

* * * * *